(12) United States Patent
Krishnan et al.

(10) Patent No.: US 8,138,153 B2
(45) Date of Patent: Mar. 20, 2012

(54) POTASSIUM CHANNEL MODULATOR PEPTIDE

(75) Inventors: Subramaniasastry Kozhalmannom Krishnan, Karnataka (IN); Padmanabhan Balaram, Karnataka (IN)

(73) Assignee: National Centre for Biological Sciences, Bangalore (IN)

( * ) Notice: Subject to any disclaimer, the term of this patent is extended or adjusted under 35 U.S.C. 154(b) by 1565 days.

(21) Appl. No.: 10/589,959

(22) PCT Filed: Oct. 8, 2004

(86) PCT No.: PCT/IB2004/003278
§ 371 (c)(1), (2), (4) Date: Aug. 18, 2006

(87) PCT Pub. No.: WO2005/085276
PCT Pub. Date: Sep. 15, 2005

(65) Prior Publication Data
US 2007/0219137 A1    Sep. 20, 2007

(30) Foreign Application Priority Data
Feb. 20, 2004  (IN) .............................. 136/CHE/2004

(51) Int. Cl.
*A61K 38/00*    (2006.01)
(52) U.S. Cl. ...................................... 514/17.4
(58) Field of Classification Search .......... None
See application file for complete search history.

(56) References Cited

OTHER PUBLICATIONS

S. Sudarslal et al. Biochem. Biophys. Res. Comm. (2004) 317, pp. 682-688.*
Y.D. Ramu et al. 3rd International Marine Biotechnology conference. (1994), Abstract.*
D. Annadurai et al. Proceedings of the National Seminar on Marine Biodiversity as a Source of Food and Medicine. (2002), Abstract.*
Terlau et al., Physiol Rev., vol. 84, No. 1, pp. 41-68, 2004.
NCBI Entrez Protein Sequence Listing: CAG10774, unnamed protein product [Tetraodon nigroviridis], retrieved from the internet Jan. 11, 2005.
Koo et al., Cellular Immunology, vol. 197, pp. 99-107, (1999).
Kurokawa et al., J. Mol. Cell. Cardiol., vol. 33, pp. 873-882, (2001).
Shah et al., Cellular Immunology, vol. 221, pp. 100-106, (2003).
Dodson et al., Trends in Neuroscience, vol. 27, No. 4, pp. 210-217, (2004).
Tamargo et al., Cardiovascular Research, vol. 62, pp. 9-33, (2004).

* cited by examiner

*Primary Examiner* — Andrew D. Kosar
*Assistant Examiner* — Thomas Heard
(74) *Attorney, Agent, or Firm* — Birch, Stewart, Kolasch & Birch, LLP

(57) ABSTRACT

A novel 13-residue peptide Mo1659 is isolated from the venom of a the cone snail, *Conus monile*. HPLC fractions of the venom extract yielded an intense UV absorbing fraction with a mass of 1659 Da. De novo sequencing using matrix assisted laser desorption and ionization and electrospray MS/MS methods with analysis of proteolytic fragments yielded the amino acid sequence, FHGGSWYRFPWGY-NH$_2$(SEQ ID NO: 1), confirmed by comparison with the chemically synthesized peptide and conventional Edman sequencing. Mo1659 has an unusual sequence with a preponderance of aromatic residues and absence of apolar, aliphatic residues like Ala, Val, Len, Ile. Mo1659 has no disulfide bridges, distinguishing it from the conotoxins and bears no sequence similarity with any of the acyclic peptides isolated thus far from cone snail venoms. Electrophysiological studies on the effect of Mo 1659 on measured currents in dorsal root ganglion neurons suggest that the peptide targets non-inactivating voltage dependent potassium channels.

3 Claims, No Drawings

SEQUENCE LISTING

```
<160> NUMBER OF SEQ ID NOS: 4

<210> SEQ ID NO 1
<211> LENGTH: 13
<212> TYPE: PRT
<213> ORGANISM: Artificial Sequence
<220> FEATURE:
<223> OTHER INFORMATION: Synthetic potassium channel inhibitor peptide
      from Conus monile
<220> FEATURE:
<221> NAME/KEY: VARIANT
<222> LOCATION: (13)..(13)
<223> OTHER INFORMATION: Optionally amidated

<400> SEQUENCE: 1

Phe His Gly Gly Ser Trp Tyr Arg Phe Pro Trp Gly Tyr
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic potassium channel inhibitor peptide
      from Conus monile
<220> FEATURE:
<221> NAME/KEY: MISC_FEATURE
<222> LOCATION: (1)..(1)
<223> OTHER INFORMATION: Xaa may be Phe or Tyr
<220> FEATURE:
<221> NAME/KEY: MISC_FEATURE
<222> LOCATION: (7)..(7)
<223> OTHER INFORMATION: Xaa may be Tyr or Phe
<220> FEATURE:
<221> NAME/KEY: MISC_FEATURE
<222> LOCATION: (8)..(8)
<223> OTHER INFORMATION: Xaa may be Arg or Lys
<220> FEATURE:
<221> NAME/KEY: MISC_FEATURE
<222> LOCATION: (9)..(9)
<223> OTHER INFORMATION: Xaa may be Phe or Tyr
<220> FEATURE:
<221> NAME/KEY: MISC_FEATURE
<222> LOCATION: (13)..(13)
<223> OTHER INFORMATION: Xaa may be Tyr or Phe and optionally amidated

<400> SEQUENCE: 2

Xaa His Gly Gly Ser Trp Xaa Xaa Xaa Pro Trp Gly Xaa
1               5                   10

<210> SEQ ID NO 3
<211> LENGTH: 8
```

```
-continued

<212> TYPE: PRT
<213> ORGANISM: Artificial Sequence
<220> FEATURE:
<223> OTHER INFORMATION: Synthetic peptide

<400> SEQUENCE: 3

Gly Gly Ser Trp Tyr Arg Phe Pro
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 4

Phe Pro Xaa Xaa
1
```

POTASSIUM CHANNEL MODULATOR PEPTIDE

FIELD OF INVENTION

This invention pertains to the field of potassium channel modulators that have utility as therapeutic molecules for diseases such as cardiac arrhythmias, multiple sclerosis, a rheumatoid arthritis and other syndromes involving defective potassium channels.

PRIOR ART

Potassium channels are membrane proteins, which determine the resting membrane potential and the duration of action potentials, involved in complex biological processes such as regulation of heart rate, muscle contraction, neuronal excitability and immune function (Kurokawa, J. et al., *Journal of Molecular and Cellular Cardiology* (2001), 33, 873-882; Dodson, P. D. and Forsythe, I. D., *Trends in Neurosciences* (2004), 27, 210-217; Koo, G. C. et al., *Cellular Immunology* (1999), 197, 99-107). They act as targets for neurotransmitters, drugs, toxins etc. and are attractive tool for rational drug design. For example, blockers of certain $K^+$ channels show class III antiarrhythmias action, a property being utilized for preventing or suppressing re-entrant arrhythmias (Tamargo, J. et al., *Cardiovascular Research* (2004), 62, 9-33). Margatoxin, a scorpion derived toxin, is reported to have a property to treat autoimmune disorders such as multiple sclerosis and rheumatoid arthritis (Shak, K et al., *Cellular Immunology* (2003), 221, 100-106). Conotoxins, peptides from cone snails, are among the most potent ligands for receptors and channels in the central nervous system. A kappa conotoxin, κ-Pviia, from *Conus purpurascens*, has been advanced as a possible candidate for treatment of Alzheimer's disease, Lambert-Eaton syndrome and myasthenia gravis (Olivera, S. M. et al., *Expert Opinion on Therapeutic Patents* (2001), 11, 603-623). Potassium channels are membrane proteins, which determine the resting membrane potential and the duration of action potentials, involved in complex biological processes such as regulation of heart rate, muscle contraction, neuronal excitability and immune function (Kurokawa, J. et al., *Journal of Molecular and Cellular Cardiology* (2001), 33, 873-882; Dodson, P. D. and Forsythe, I. D., *Trends in Neurosciences* (2004), 27, 210-217; Koo, G. C. et al., *Cellular Immunology* (1999), 197, 99-107). They act as targets for neurotransmitters, drugs, toxins etc. and are attractive tool for rational drug design. For example, blockers of certain $K^+$ channels show class III antiarrhythmias action, a property being utilized for preventing or suppressing re-entrant arrhythmias (Tamargo, J. et al., *Cardiovascular Research* (2004), 62, 9-33). Margatoxin, a scorpion derived toxin, is reported to have a property to treat autoimmune disorders such as multiple sclerosis and rheumatoid arthritis (Shak, K et al., *Cellular Immunology* (2003), 221, 100-106). Conotoxins, peptides from cone snails, are among the most potent ligands for receptors and channels in the central nervous system. A kappa conotoxin, κ-Pviia, from *Conus purpurascens*, has been advanced as a possible candidate for treatment of Alzheimer's disease, Lambert-Eaton syndrome and myasthenia gravis (Olivera, B. M. et al, *Expert Opinion on Therapeutic Patents* (2001), 11, 603-623).

The molecular diversity of $K^+$ channels is larger than any other group of ion channels, with more than 80 different genes and many splice variants. The diversity is strikingly observed in the central nervous system, with numerous subtypes of neurons expressing a unique set of potassium channels. The voltage gated potassium channels are responsible for the repolarization of the action potential in neurons. Earlier electrophysiological studies on dorsal root ganglion neurons have indicated the expression of at least six voltage gated $K^+$ currents, three transient and three non-inactivating currents.

SUMMARY OF INVENTION

The instant invention claims novel potassium channel modulating activity for a 13-residue peptide obtained from *Conus monile*. The target sequence has been prepared by conventional solid phase peptide synthesis procedure and found identical to the natural peptide. Analogues of this peptide sequence can be readily prepared by synthetic methods.

Electrophysiological studies suggest that Mo 1659, a 13-residue peptide, specifically acts on the non-inactivating $K^+$ currents. Studies with cloned $K^+$ channels and investigations of synthetic analogues are necessary to identify the target channel subtype and to establish the molecular mechanism of channel blocking activity.

DETAILED DESCRIPTION OF INVENTION

The instant invention discloses a substantially pure peptide having the amino acid sequence FHGGSWYRFPWGY (SEQ ID NO: 1).

The peptide is used a potassium channel modulator.

A process of preparing substantially pure peptide comprising of:
(i) isolation of the peptide, and
(ii) purifying the peptide by chromatographic methods.

The peptide in step (i) is isolated from venoms of *Conus monile*.

The purification step (ii) is carried out by HPLC (High Performance Liquid Chromatography).

The peptide is used for treatment neurophysiological and neurological disorders.

The peptide is used for treatment neurophysiological and neurological disorders n schizophrenia, epilepsy, bipolar disorder or in syndromes that affect the nervous system. A pharmaceutical composition comprising a peptide having the amino acid sequence FHGGSWYRFPWGY (SEQ ID NO: 1) with or without pharmaceutically acceptable carriers.

The invention will now be discussed in the following examples, not to be considered as limiting.

EXAMPLES

Example 1

Isolation and Purification of Peptide

The specimen, *Conus monile* was collected from the southeast coast of India. The venom ducts after dissection were preserved in ethanol and the venom that oozes out was subjected to High Performance Liquid Chromatography (HPLC) purification after concentration on a rotavapor. Crude venom extract was applied onto a Jupiter 4μ, Proteo 90 Å, $C_{18}$ column (10 mm×250 mm) and eluted with a linear gradient of acetonitrile containing 0.1% TFA. The flow rate was maintained at 1 ml $min^{-1}$ and the absorbance was monitored at 226 nm. Fractionation into several peptide components was achieved. The peptide components were analyzed by MALDI mass spectra analysis of individual HPLC fractions. The intense component at the retention time of 23.4 minutes corresponding to a molecular mass of 1659 Da was chosen for mass spectrometric denovo sequencing. The peptide component showed a high resolution MALDI mass spectrum, which establishes [M+H]+=1659.1 Da (monoisotopic mass). The +2 and +3 states are detectable suggesting the presence of at least three protonatable groups in the molecule. Attempted reduction with DTT followed by alkylation with iodoacetamide left the molecular mass unchanged, establishing the absence of disulfide bonds. Acetylation with acetic anhydride and acetic acid yielded a product with a mass [M+H]+=1701.3 Da (Δm=+42 Da) indicating the presence of a single primary amino group. UV and fluorescence spectra established the presence of both Trp and Tyr residues. Peptide sequencing was undertaken using MALDI MS/MS techniques selecting the 1659.1 Da as the precursor ion. The presence of an intense b2 ion at 285 Da permitted sequential tracing of the 8-residue segment -GGSWYRFP- (residues 3 to 10 of SEQ ID NO: 1). The immonium ions at 70, 110, 136 and 159 suggested the presence of the residues Pro, His, Tyr and Trp, respectively. The b2 ion at 285 Da could correspond to the dipeptide -FH- or -HF- at the amino terminus. The observation of mass peaks at 194.9 Da suggested the presence of the dipeptide ion -GH- or -HG-. This supports the assignment of the sequence -FHG- at the N-terminus. The paucity of intense fragments in the mass range 1200-1500 Da limited extension of the sequence at the C-terminus.

Example 2

Conformation of the Peptide

Confirmation of the determined sequence was achieved by two independent methods. First, a synthetic peptide corresponding to the determined sequence of Mo1659 was prepared and its MS/MS fragmentation pattern shown to be identical to that of the natural product. The identity of the synthetic and natural peptides was also established by HPLC analysis. Second, conventional Edman sequencing using an automated sequenator confirmed the sequence. A notable feature of Mo1659 is the presence of as many as seven aromatic amino acids (F-2, Y-2, W-2, H-1) in a short stretch of 13 residues. The positively charged peptide is notably deficient in the common aliphatic, hydrophobic amino acids like Ala, Val, Leu and Ile.

Example 2(a)

Reduction and alkylation: The purified peptide was dissolved in 30 μL, 0.05 M $NH_4HCO_3$ buffer, pH 8.0. For the reduction, 200 mM stock dithiothreitol (DTT) was added to a final concentration of 8 mM and incubated at 37° C. for 2 h followed by addition of iodoacetamide stock solution, to get a final concentration of 40 mM. The resulting mixture was incubated at room temperature in the dark, for 1 h and subsequently analyzed by MALDI MS.

Acetylation: The peptide solution was dried and resuspended in a 1:1 ratio of acetic acid and acetic anhydride. After 5 min of incubation at room temperature, the resultant solution was again dried and resuspended in 0.1% TFA and acetonitrile in the ratio 1:1 (v/v) and analyzed using MALDI MS. Trypsin digestion The purified sample was digested with TPCK treated trypsin (Sigma Co., USA) with 10 μg of enzyme in 50 μl of 50 mM $NH_4HCO_3$, pH 8.0 for 3 h at 37° C. The digest was analyzed using MALDI and ESI mass spectrometers.

Trypsin digestion: The purified sample was digested with TPCK treated trypsin (Sigma Co., USA) with 10 μg of enzyme in 50 μl of 50 mM $NH_4CO_3$, pH 8.0 for 3 h at 37° C. The digest was analyzed using MALDI and ESI mass spectrometers.

Digestion of Mo 1659 with trypsin yielded two fragments with masses (MALDI) 1010 Da and 668 Da, corresponding to the N-terminus and C-terminus fragments, respectively. The 668 Da fragment is assigned to the C-terminus fragment -FPXX (SEQ ID NO: 4), which has previously been detected as a fragment ion [Note that 17 Da (OH) is added to the N-terminus fragment and 1 Da (H) to the C-terminus fragment, upon hydrolysis]. The 668 Da fragment was subjected to high-energy collision induced dissociation (CID) in an ion trap mass spectrometer, using an electrospray ionization source. The intense peak at 651 Da corresponds to a facile loss of NH3 from the C-terminus suggestive of the presence of C-terminal amidation. *Conus* peptides are often posttranslationally modified, with amidation being commonly observed (14,15). The identification of the b2 ion at 245 Da corresponds to the -FP- fragment, already established by MALDI MS/MS, permitting the ready identification of the C-terminus tripeptide as -WGY-amide. The final determined sequence is FHGGSWYRFPWGY-NH2 (SEQ ID NO: 1), corresponding to a calculated average mass of 1659.8 Da (Average mass observed in ESI MS=1659.3 Da).

Mass spectrometry: Electrospray ionization (ESI) mass spectra were obtained on a Hewlett Packard, HP 1100 MSD series spectrometer equipped with a single quadrupole analyzer. The data were acquired over a range of 300 to 1500 m/z in positive ion mode and analyzed using HP LC/MSD Chemstation software. MALDI spectra were collected using a Bruker Daltonics, Ultraflex TOF/TOF system, in the reflectron positive ion mode, equipped with a nitrogen laser of 337 nm. The samples were prepared by mixing equal volumes of peptide solution and saturated matrix (α-cyano-4-hydroxy cinnamic acid). A standard peptide mixture was used for external calibration. ESI MS/MS data were obtained on Esquire 3000 plus LC ion trap mass spectrometer (Bruker Daltonics, Germany). The nitrogen gas pressure and flow rate to the nebulizer were 10 bar and 5 l $min^{-1}$, respectively with a drying gas temperature of 300° C., The scan range was set at 50 to 1000 m/z. The sample was dissolved in 1:1(v/v) ratio of water and acetonitrile containing 0.1% HCOOH and was infused directly into the system delivered by a syringe pump (Cole-Parmer, Vernon Hills, Ill., USA) at a flow rate of 120 μl h-1. Helium was used as the collision gas for CID experiments. The data were analyzed using Esquire data analysis software, version 3.1.

Edman sequencing: The primary sequence of the peptide was determined by using a Shimadzu PPSQ-10 protein sequencer equipped with an LC-10A HPLC system.

Example 3

Confirmation of Mo 1659 Sequence

Confirmation of the determined sequence was achieved by two independent methods. First, a synthetic peptide corresponding to the determined sequence of Mo1659 was prepared and its MS/MS fragmentation pattern shown to be identical to that of the natural product. The identity of the synthetic and natural peptides was also established by HPLC analysis. Second, conventional Edman sequencing using an automated sequenator confirmed the sequence. A notable feature of Mo1659 is the presence of as many as seven aromatic amino acids (F-2, Y-2, W-2, H-1) in a short stretch of 13 residues. The positively charged peptide is notably deficient in the common aliphatic, hydrophobic amino acids like Ala, Val, Leu and Ile.

Example 4

Novelty of the Conopeptide Mo 1650

A search of the existing protein sequence databases reveals no matches for the determined sequence of Mo1659. The uniqueness of the peptide is established through different database searches, using different algorithms like Blast, BlastP etc as described below:
Uniqueness of the sequence: FHGGSWYRFPWGY (SEQ ID NO: 1)
Uniqueness of the sequence FHGGSWYRFPWGY (SEQ ID NO: 1) was shown in the following ways:
Prosite was used to search for the sequence:

```
F-H-G-G-S-W-Y-R-F-P-W-G-Y       (SEQ ID NO: 1)
```

This sequence was searched for in PDB, Swissprot, TrEMBL, TrEMBL new. No hits were found.
Prosite was also used to search for the following variant: [FY]-H-G-G-S-W-[YF]-[RK]-[FY]-P-W-G-[YF] (SEQ ID NO: 1)
No hits were found.

Example 5

Assay for Potassium Channel Activation of Peptides

DRG neuron preparation Dorsal root ganglion (DRG) neurons for electrophysiological studies were prepared as follows:

$5^{th}$ Postnatal day male Wistar rats were anesthetized with diethyl ether. The whole vertebral column was removed and transferred to a dish containing pre-oxygenated phosphate buffered saline. While holding the vertebral column a strip of bone from the dorsal root of the vertebral column was cut. The dorsal root ganglia together with dorsal and ventral roots were individually taken out with fine dissecting forceps and transferred into phosphate buffered saline containing 1.5 mg ml$^{-1}$ trypsin (from porcine pancreas, Sigma, USA). The DRGs were minced with dissecting spring scissors, and incubated at 37° C. for 30 min. After trypsin treatment, the cells were pelleted by centrifugation at 1000 rpm. for 5 min. The supernatant was removed, and washed with 1 ml of DMEM containing 10% FBS. Following resuspension in fresh DMEM containing 10% FBS, single cell suspension was obtained by trituration using a fire polished Pasteur pipette. To increase the cell density, a locally fabricated 8 mm diameter optically polished glass ring was placed on the bottom of a sterile 35 mm tissue culture dish. The suspended cells were plated into the well formed by the glass ring. The cells were incubated for 1 h at 37° C. Isolated DRG neurons were used for the electrophysiology experiments.

Electrophysiology: Isolated K$^+$ currents were recorded from DRG neurons using the patch-clamp technique in the whole-cell mode using an EPC-8 amplifier (Heka). Patch-clamp electrodes with resistance of 1-3 mega-ohm were made from borosilicate glass (Clark Electromedical Instruments, UK). The external bath solution contained: 130 mM choline chloride, 3 mM KCl, 2.5 mM CoCl$_2$, 0.6 mM MgCl$_2$, 10 mM Hepes, 1.2 mM NaHCO$_3$ and 10 mM glucose, pH 7.4 with Tris base; osmolarity, 325 mosmol adjusted with sucrose. The internal solution contained: 140 mM KCl, 1 mM CaCl$_2$.2H$_2$O, 2 mM MgCl$_2$.6H$_2$O, 11 mM EGTA, 10 mM Hepes, pH 7.2 with Tris base; osmolarity 310 mosmol. The neurons were voltage-clamped at −80 mV in all the experiments. Capacity and leak subtraction was done using a P/4 subtraction protocol. Using Rs compensation of 50% in all the experiments minimized voltage errors. Data acquisition and pulse protocols were controlled with the pClamp8 software, and Digidata 1320 analog/digital converter (Axon Instruments Inc.). The bath temperature was maintained at 20° C. The toxin was dissolved in water. Bolus application of the toxin was employed to achieve a final bath concentration of 200 nM. The effects of Mo 1659 on the K$^+$ currents reported here were recorded 15 min after peptide application.

Mo1659 shows K$^+$ channel modulating activity in DRG neurons. A marked reduction in the current amplitudes at all the potentials was observed with 200 nM of the Mo1659 in the external bath solution. The mixed K$^+$ currents have a fast transient current and a sustained current component. The fast transient current component was dissected from the sustained current component using two different pre-pulse voltages followed by identical voltage protocols. Although the K$^+$ current components cannot be fully isolated using the conditioning prepulse voltages alone (18), the results suggest that Mo1659 addition to the external bath solution predominantly affects the sustained K$^+$ current component. It may be noted that the transient current component, that was obtained following subtraction of current traces, is not significantly affected by Mo1659. Similar results were obtained in 5 different experiments. Mo1659 thus appears to affect non-inactivating voltage dependent potassium channels. The reduction of total K$^+$ currents in excitable cells by blocking potassium channels is a process, which is important in developing therapeutics for arrhythmias and heart failure. Enhancing the duration of action potentials using potassium channel blockers is a possible strategy for the development of new classes of antiarrhythmic agents.

Example 6

Process of Producing Monile Peptide Mo 1659

Purification from the snail venom: The specimen, *Conus monile* was collected from the southeast coast of India. The venom ducts after dissection were preserved in ethanol and the venom that oozes out was subjected to High Performance Liquid Chromatography (HPLC) purification after concentration on a rotavapor. Crude venom extract was applied onto a Jupiter 4μ, Proteo 90 Å, C$_{18}$ column (10 mm×250 mm) and eluted with a linear gradient of acetonitrile containing 0.1% TFA. The flow rate was maintained at 1 ml min$^{-1}$ and the absorbance was monitored at 226 nm. The intense component at the retention time of 23.4 minutes is the desired Mo1659 peptide. The homogeneity of this fraction was demonstrated by re analysis using HPLC on an analytical column (Zorbax C18 RP, 300 Å pore size, 5μ particle size). Furthermore, identity of the peptide and the absence of contaminants were demonstrated by LC-ESI and MALDI mass spectrometry.

The peptide thus obtained is tested for electrophysiological activity and stored at +4° C. for further use.

Example 7

Chemical Synthesis of Monile Peptide, Mo1659

The peptide was synthesized by standard solid phase peptide synthetic methods using Fmoc chemistry. All amino acids are protected at the N-terminus with the Fmoc group (Nova Biochem). The side chains of Tyr and Ser were protected with the t-Bu group, Arg with Mtr group, His with trityl group. The coupling reactions proceeded using the OPfp esters of the protected amino acids on Fmoc-Rink amide AM resin (200-400 mesh, Nova Biochem). The synthesis was performed with 300 mg of resin with a bead capacity of 0.63 mMg$^{-1}$. The C-terminal amino acid (Tyr) was linked to the resin by the formation of an amide linkage with the amino functional group emanating from the solid support. Ser and His were coupled by using HBTU (N-[(1H-benzotriazol-1-yl)(dimethylamino)methylene]-N-methylmethanaminium hexafluoro phosphate N-oxide). The Fmoc deprotections were performed with 20% piperidine in dimethylformamide. Peptide was cleaved from 100 mg of resin after synthesis, using 94% TFA (7.52 ml), containing 5% anisole (400 µl) and 1% ethanedithiol (80 µl) as cation scavengers. After 5-6 h, the resin was filtered off, the TFA was removed by evaporation in vacuo and the peptide was precipitated with ether. The precipitate was repeatedly washed with ether and purified by RP HPLC.

It is also possible to produce this peptide by recombinant DNA technology taking advantage of the fact that this invention describes the peptide sequence and based on which DNA sequence can be derived from the known triplet codes for each amino acid. The DNA sequence thus obtained can be synthesized/relevant gene stretch can be obtained from the snail DNA using methods such cDNA cloning, Polymerase chain reaction etc and cloned into expression vectors either in prokaryotic or eukaryotic systems. The clones thus obtained can be engineered to produce the peptide Mo 1659 by known methods and purified to homogeneity by known methods.

We claim:

1. An isolated peptide having an amino acid sequence FHGGSWYRFPWGY as shown in SEQ ID NO: 1, wherein the peptides is a potassium channel modulator.

2. The isolated peptide of claim 1, wherein the peptide is synthetically produced.

3. A pharmaceutical composition comprising, as an active ingredient, the isolated peptide of claim 1 together with one or more pharmaceutically acceptable carriers or excipients.

* * * * *